(12) United States Patent
Freedman et al.

(10) Patent No.: US 7,683,613 B2
(45) Date of Patent: Mar. 23, 2010

(54) HIGH PRESSURE/HIGH TEMPERATURE MAGNETIC RESONANCE TOOL

(75) Inventors: Robert Freedman, Houston, TX (US); Krishnamurthy Ganesan, Sugar Land, TX (US); Douglas W. Grant, Austin, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 117 days.

(21) Appl. No.: 11/942,534

(22) Filed: Nov. 19, 2007

(65) Prior Publication Data

US 2009/0128144 A1    May 21, 2009

(51) Int. Cl.
*G01V 3/00* (2006.01)
(52) U.S. Cl. ...................... 324/306; 324/303
(58) Field of Classification Search ............. 324/306, 324/303
See application file for complete search history.

(56) References Cited

U.S. PATENT DOCUMENTS

| | | | | |
|---|---|---|---|---|
| 4,110,680 | A | * | 8/1978 | Bergmann et al. ......... 324/306 |
| 4,638,251 | A | * | 1/1987 | King .......................... 324/306 |
| 4,782,295 | A | * | 11/1988 | Lew ............................ 324/306 |
| 4,785,245 | A | | 11/1988 | Lew et al. |
| 6,111,408 | A | | 8/2000 | Blades et al. |
| 6,346,813 | B1 | | 2/2002 | Kleinberg |
| 6,737,864 | B2 | | 5/2004 | Prammer et al. |
| 6,938,469 | B2 | | 9/2005 | Ganesan |
| 6,952,096 | B2 | | 10/2005 | Freedman |
| 7,053,611 | B2 | | 5/2006 | Freedman |
| 2005/0030034 | A1 | | 2/2005 | Ganesan |
| 2005/0270023 | A1 | | 12/2005 | Freedman |
| 2006/0020403 | A1 | | 1/2006 | Pusiol |
| 2007/0114996 | A1 | | 5/2007 | Edwards |

* cited by examiner

*Primary Examiner*—Louis M Arana
(74) *Attorney, Agent, or Firm*—Darla P. Fonseca; Dave R. Hofman

(57) ABSTRACT

The present invention pertains to an apparatus and method for conducting magnetic resonance measurements on fluids at high pressures and/or high temperatures. The apparatus can be used in conjunction with or as part of a downhole fluid sampling tool to perform NMR measurements on fluids withdrawn from petroleum reservoirs, or can also be used for laboratory measurements on live reservoir fluids. The apparatus can perform all of the measurements made by modern NMR logging tools, including multi-dimensional distribution functions of spin-spin ($T_2$) and spin-lattice relaxation ($T_1$) times and molecular diffusion coefficients. The spin densities of hydrogen and other NMR sensitive species can be computed from the distribution functions. The apparatus can also be used to predict the apparent conductivity of the fluids in the flowline from measurements of the quality factor ("Q") of the NMR circuit. The apparent conductivity can be used to predict water cut or water salinity.

21 Claims, 2 Drawing Sheets

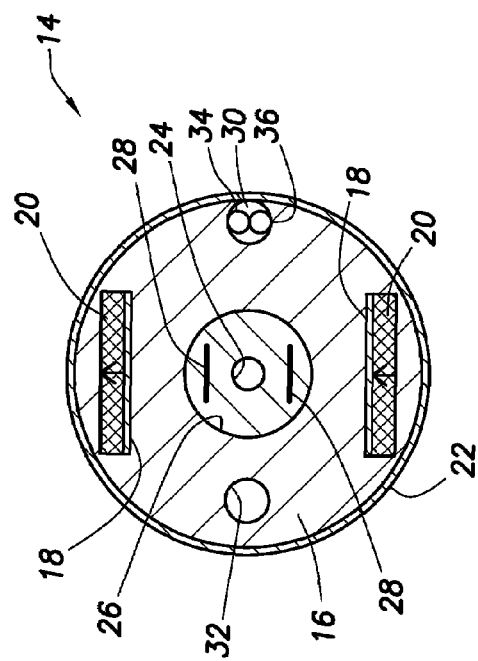
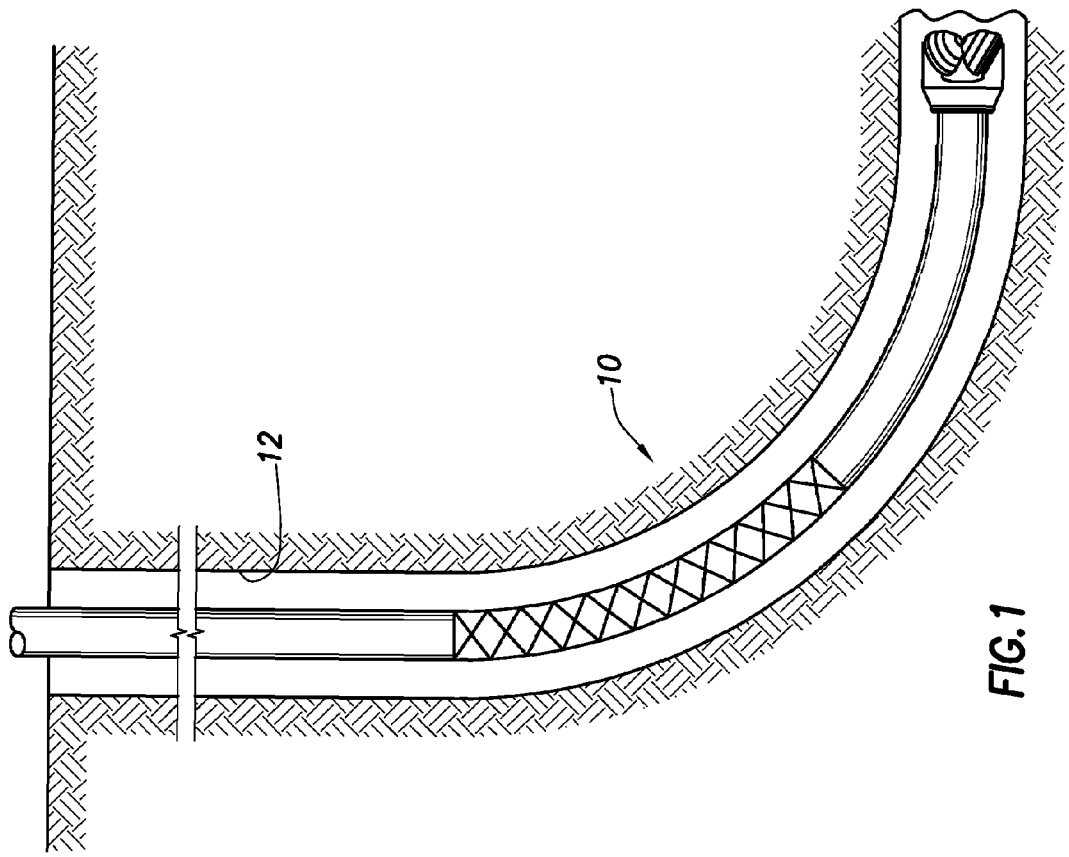

HIGH PRESSURE/HIGH TEMPERATURE MAGNETIC RESONANCE TOOL

TECHNICAL FIELD

The present invention pertains to making NMR (nuclear magnetic resonance) or ESR (electron spin resonance) measurements on fluids that are at high pressure and/or high temperature.

BACKGROUND OF THE INVENTION

In the field of hydrocarbon exploration, measurements are often made on reservoir fluids. Such measurements are typically made to obtain information on different reservoir fluid properties, e.g., resistivity, NMR, optical absorption and scattering, dielectric constant, etc. Measurements may be made on fluids in the formation or in a flowline of a fluid sampling tool. Fluid sampling tools are widely used in the well-logging industry. Borehole fluid sampling tools have one or more probes that are pressed against the borehole wall so that reservoir fluids can be pumped out of the earth formation into a flowline or sample bottle situated in the fluid sampling tool. A sample placed in a sample bottle may be preserved so that it may be tested in a laboratory (i.e., a "live oil" sample).

Fluid sampling tools may be used to measure reservoir pressures. Those tools often operate in high pressure and high temperature environments. The pressure of reservoir fluids in a flowline can exceed 25,000 pounds per square inch (psi), and temperatures can approach or even exceed 200° C. Because of the high temperatures and pressures, the flowlines used in commercial fluid sampling tools are typically made of stainless steel or some other suitable metal alloy.

A commercially available, NMR-compatible pressure cell for laboratory use exists in the prior art and is frequently used in conjunction with a 2 MHz laboratory NMR instrument to perform NMR measurements on fluid (e.g., oil) samples at elevated temperatures and pressures. In the laboratory apparatus, the NMR radio frequency (RF) coil used to excite the protons in the reservoir fluids is situated outside of the pressure cell. The pressure cell is made of a non-conductive and non-magnetic plastic. The internal pressure on the inner walls of the pressure cell is at least partially offset by a pressurized, NMR-insensitive fluid contained outside the cell. The pressurized fluid reduces the net pressure on the inner walls of the pressure cell, and can also be heated to regulate the temperature of the sample. This type of pressure cell is not, however, viable for use in a downhole fluid sampling tool because it is incapable of operating at the elevated temperatures and pressures encountered in a wellbore.

The RF antenna used in the above pressure cell is a solenoidal coil that is located outside of the pressure cell and encircles the sample. The fluid sample only partially occupies the interior region of the RF coil. This results in a reduced "fill factor", in this case on the order of 0.3. The low fill factor is problematic because the signal-to-noise ratio (S/N) of the NMR measurement is directly proportional to the fill factor. Another problem with the prior art pressure cell is that it requires pressure compensation, as described above, which adds to the complexity, cost, and maintenance of the tool. One apparatus using such a pressure cell has maximum pressure and temperature ratings of 10 Kpsi and 260° F., respectively. Those maximum ratings are far too low for modern fluid sampling logging tools that must be able to analyze fluids at temperatures and pressures in the neighborhood of 30 Kpsi and 400° F., respectively.

U.S. Pat. No. 4,785,245 (the '245 patent) issued to Lew et al. discloses a NMR device for monitoring the fraction of oil in a multi-phase flow stream coming from a producing oil reservoir. The '245 patent discloses a non-metallic flow pipe that has a RF receiver coil and a separate transmitter antenna, both mounted on the outer surface of the flow pipe. The flow pipe is made from ceramic or other non-conductive and non-magnetic material. The NMR magnet, flow pipe, and associated antennas disclosed in the '245 patent, however, are not capable of making NMR diffusion measurements, and are not suitable for the high pressure and temperature environment encountered by borehole fluid sampling tools.

Prammer et al., in U.S. Pat. No. 6,737,864 (the '864 patent) issued to Halliburton Energy Services, Inc., discloses a NMR device for use in a fluid sampling logging tool. The '864 patent uses a flow tube made from ceramic, glass, or plastic. Those materials do not have the strength to withstand the pressures encountered in typical downhole environments. Moreover, the RF coil is outside of the flow tube, which limits the S/N of the measurement, and there are no gradient coils for Pulsed Field Gradient (PFG) diffusion measurements.

Kleinberg, in U.S. Pat. No. 6,346,813 (the '813 patent, assigned to the assignee of the present invention), discloses a NMR module for a fluid sampling logging tool. Kleinberg recognized that a metal flowline attenuates electromagnetic (EM) radiation from antennas or other transmitters situated outside of the flowline. The attenuation caused by metallic or highly conductive steel flowlines causes severe signal-to-noise ratio problems for measurements made by EM sensors situated outside of the flowline. The '813 patent discusses, among other things, a metal flowline with a RF coil located in the interior region of the flowline. The flowline is enclosed by a permanent magnet; specifically, a circular Halbach magnet configuration that surrounds the flowline. However, certain features of the present invention are not disclosed by Kleinberg. For example, the '813 patent does not teach that the PFG coils can be advantageously located outside of the metal flowline without comprising diffusion measurements.

The '864 patent and U.S. Pat. No. 6,111,408 issued to Blades and Prammer disclose two types of magnet assemblies wherein the magnet surrounds the flowline. Both patents disclose a circular Halbach magnet design that consists of an array of eight magnet pieces surrounding the flowline. The magnetization direction of each magnet piece is different, i.e., it increases by 90° going clockwise from one piece to the next. In theory, this design produces a relatively homogeneous magnetic field over the measurement region. However, in practice it is difficult to manufacture this magnet and small deviations of the directions of the magnetization or field strength from those prescribed by theory can result in a substantial gradient in the magnetic field in the region of the flowline. The '864 patent also discloses a circular array of eight magnetic dipoles that surround the flowline.

The magnet designs disclosed in the prior art patents on NMR magnets for borehole fluid sampling and pressure tools have several shortcomings. For example, prior art magnet designs that have magnets surrounding the flowline do not provide space for "thru-wires". Thru-wiring is required for combinability of a NMR measurement module with other measurement modules. Moreover, prior art designs do not provide for continuous flow within or through the sampling tool when NMR measurements are desired on a stationary sample. For example, NMR diffusion measurements are preferably made on fluids that are stationary (non-flowing). In such instances, the prior art devices require the flow (pumping) be stopped while NMR measurements are performed. By having separate flowlines for the sample and through-put fluids, through-put fluids can be pumped through a flowline without interruption while acquiring NMR data on stationary fluids in a NMR measurement flowline.

BRIEF SUMMARY OF THE INVENTION

The present invention pertains to an apparatus and method for conducting magnetic resonance measurements on fluids at high pressures and/or high temperatures. The apparatus can be used in conjunction with or as part of a downhole fluid sampling tool to perform NMR measurements on fluids withdrawn from petroleum reservoirs, or can also be used for laboratory measurements on live reservoir fluids. The apparatus can perform all of the measurements made by modern NMR logging tools, including multi-dimensional distribution functions of spin-spin ($T_2$) and spin-lattice relaxation ($T_1$) times and molecular diffusion coefficients. The spin densities of hydrogen and other NMR sensitive species can be computed from the distribution functions. The apparatus can also be used to predict the apparent conductivity of the fluids in the flowline from measurements of the quality factor ("Q") of the NMR circuit. The apparent conductivity can be used to predict water cut or water salinity.

BRIEF DESCRIPTION OF THE DRAWINGS

The novel features that are believed to be characteristic of the invention, both as to its organization and method of operation, will be better understood from the following description when considered in conjunction with the accompanying figures. It is to be expressly understood, however, that each of the figures is provided for the purpose of illustration and description only, and is not intended to limit the scope of the present invention.

FIG. 1 is an illustration of an embodiment of a high pressure/high temperature magnetic resonance tool disposed in a wellbore, in accordance with the present invention.

FIG. 2 shows an end view of one embodiment of a magnet assembly used in the high pressure/high temperature magnetic resonance tool of FIG. 1.

DETAILED DESCRIPTION OF THE INVENTION

Figure 3:
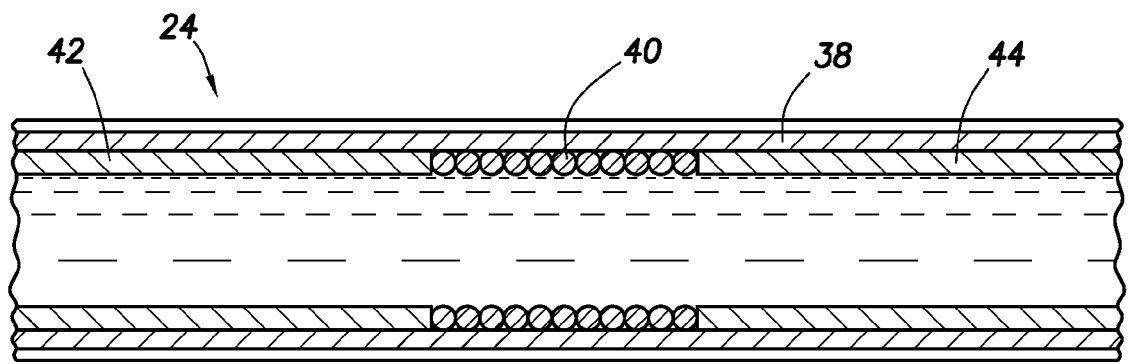
FIG. 3 shows an embodiment of a flowline having a RF coil in its interior region, and used in the high pressure/high temperature magnetic resonance tool of FIG. 1.

FIG. 1 shows a magnetic resonance tool 10 disposed in a wellbore 12. The tool could be a nuclear magnetic resonance tool or an electron spin resonance tool. Also, although the particular embodiment shown is in a wellbore, the invention is not limited to downhole applications and may be used in a laboratory. While one embodiment of this invention provides for a NMR instrumented flowline section that can be used in a logging tool, the same apparatus can also be used as a high pressure cell for conducting laboratory NMR measurements on reservoir or process fluids. "Process fluids" are any of the intermediate or final fluids resulting from performing a process. The invention may be used in wireline logging or while-drilling.

FIG. 2 discloses a NMR module having a magnet assembly 14 that can be used to perform NMR spin echo measurements to determine, for example, relaxation time and diffusion coefficient distributions of reservoir fluids. The fluids of interest may be in a laboratory environment, a process environment, a tank, or a flowline or sample container of a borehole fluid sampling and pressure tool. Laboratory and process environments can, like downhole tool environments, present challenges due to high temperature, high pressure, and corrosion. Downhole tools, however, impose additional space limitations due to the limited wellbore diameter. Placement of the NMR module in the limited space available in a downhole fluid sampling tool poses a number of challenges.

The sampling tool typically pumps fluid from the formation into a flowline or sample container. Many measurement modules may be placed along the fluid flow path, one of which may be a NMR module. The NMR module shown in FIG. 2 comprises magnet assembly 14 and associated electronics (not shown). The magnet assembly 14 comprises a magnet carrier 16, magnet pole pieces 18, magnets 20, and a magnet cover 22.

The magnet assembly 14 shown uses two parallel magnetic plates 20 that are magnetized in the direction transverse to a first flowline 24, though the invention could also employ electromagnets. In contrast to the Halbach design used in prior art, this choice of magnet 20 is very simple to model and manufacture, and is very economical. This configuration of the magnets 20 allows for several improvements over the prior art magnet designs in which the magnets encircle the flowline. For example, as shown in FIG. 2, there is ample space in a central bore 26 of the magnet carrier 16 for both a flowline 24 and external pulsed field gradient (PFG) coils 28. This design also provides additional space on the sides of the central bore 26 for two passageways 30, 32 that can be used to pass a thru-wiring bundle and one or more additional flowlines 34, 36.

The magnet carrier 16 is preferably made from non-magnetic stainless steel. Upper and lower magnets 20 reside on opposite sides of the magnet carrier 16. The magnets 20 are preferably made from multiple pieces of samarium-cobalt that are sandwiched between two plates of non-magnetic stainless steel for mechanical integrity. The mechanical integrity of the magnets 20 is further insured by injecting a resin or potting material into the void space between the magnet pieces. This helps to prevent the magnet pieces from moving due to vibration and shock. The choice of magnet materials can be altered within the scope of the invention. For example, a neodymium-iron-boron magnet material could be used for the magnet. However, that magnet would be more temperature sensitive than a samarium-cobalt magnet.

It is understood that each of the magnets 20 shown in FIG. 2 will in practice comprise multiple smaller magnets whose sizes, shapes, numbers, and arrangements depend on the specific magnet material properties and the desired magnetic field strength and field gradient over a prescribed volume of the measurement region. The multiple pieces may also be encased within a protective enclosure. The multiple-piece construction of the magnet allows for easy variation of different dimensional parameters that help tailor the strength and homogeneity of magnetic field in the measurement region. However, the multiple pieces usually have slightly different magnetic field strength and/or magnetization direction that tends to make the magnetic field less homogeneous in the desired region. This problem is mitigated using pole pieces 18 described below.

To achieve a low magnetic field gradient over the sample, it is customary to homogenize the magnetic field by placing permeable metal plates 18, referred to as "pole pieces", on or near the faces of the magnets 20 as shown in FIG. 2. Pole pieces 18 made, for example, from magnetic stainless steel plates are situated between the magnet 20 and the magnet carrier 16. The pole pieces 18 can also be constructed from magnetic cold roll steel or other suitable material having a high magnetic permeability. The shape, position, and size of the pole pieces 18 are tailored to achieve the desired field homogeneity over the sample volume.

The magnet carrier 16 has two flow paths defined by two or more flow tubes. The first flow tube 24, shown centrally located in the central bore 26 of the magnet carrier 16 and along the longitudinal axis of the NMR module, allows the fluid to enter the primary measurement region of the NMR module. It is in this region that NMR spin-echoes are created and detected by applying radiofrequency (RF) and PFG pulses. The fluid in the first flow tube 24 can be regulated to flow at some desired rate or may be completely stopped within the flow tube 24 while NMR measurements are performed. For example, diffusion measurements are preferably made on stopped fluid, while relaxation time measurements can be made on flowing or stopped fluid. Velocity profile measurements can be made on flowing fluid. U.S. Pat. No. 6,952,096 teaches how to determine velocity profiles from NMR measurements and is incorporated by reference for all purposes.

The second flow tube (or a plurality of separate flow tubes) 34, 36 in passageway 30, shown laterally offset from the longitudinal axis of the NMR module, allows fluid to flow though the NMR module in a relatively unrestricted manner. That allows, for example, other modules in the sampling tool to receive fluid on which to perform their respective analyses while NMR measurements are made on stopped fluid. Thus, even when the fluid in the first flow tube 24 is stopped, pumping can continue, and fluid may continue to flow through the second flow tube 34. If a plurality of flow tubes 34, 36 is used, different fluids, for example, coming from different probes, can pass separately within the separate flow tubes 34, 36.

In addition, FIG. 2 shows a bore 32 in the NMR module, laterally offset from the longitudinal axis of the NMR module, through which wires can pass. Those wires are commonly known as "thru-wires" and typically carry signal and power. This allows the NMR module to be placed at various locations within the sampling tool or for other tools to be placed below the sampling tool and be operable. Typical prior art magnet designs such as the Halbach design can not accommodate additional flowlines or thru-wires.

In one embodiment of the invention (FIG. 3), the first flow tube 24 is a cylindrically shaped metal tube. The first flowline 24 is a relatively short section that is connected on both ends to the second flowline 34, and preferably has one or more valves to regulate flow through first flowline 24. The diameter, wall thickness, and material of the flow tube is chosen to meet the pressure and temperature specifications of the NMR module. The first flow tube 24 can be made from non-metallic materials if the particular material used can withstand the temperatures and pressures encountered, for example, in a wellbore, but is considered to be metallic in the following discussion. The structural integrity provided by such materials eliminates the need for pressure compensation.

A thin-walled, non-conductive stand-off sleeve 38 is disposed in the interior region of the first flow tube 24 and extends along the length of the first flow tube 24. The stand-off sleeve 38 provides a separation or stand-off of the RF coil 40 (described below) from the wall of the conductive metal tube. The stand-off helps reduce the effect of eddy currents in the metal flow line 24. The stand-off is typically very thin, on the order of a few millimeters thick. Using a thin-walled stand-off sleeve 38 allows the antenna coil 40 to encircle as much of the sample as possible, providing a coil fill factor of nearly one and enhancing the Q-factor of the RF antenna. That improves the S/N of the NMR measurements as compared to when the RF coil 40 is placed directly in contact with the metal flowline 24. The stand-off material is preferably non-conductive and non-magnetic, provides resistance to corrosive reservoir fluids, and does not have a NMR signal. U.S. Pat. No. 6,938,469 teaches determining sample conductivity from NMR Q-measurements and is incorporated by reference for all purposes.

A cylindrically shaped RF solenoid antenna coil 40 is also disposed in the interior region of the first tube 24 and circumferentially adjacent the non-conductive stand-off sleeve 38. Two short, thin-walled, non-conductive positioning sleeves 42, 44 are disposed in the interior region of the first tube 24, one on each end of the RF coil 40 to help secure the RF coil 40 and provide wear-protection from flowing fluids. One or both of the non-conductive positioning sleeves 42, 44 is grooved so that wires from the RF coil 40 can be routed to an end of the first flow tube 24 and passed outside the first flow tube 24 through a pressure-sealing feed through. A thin layer of stand-off material is preferably disposed on the inner diameter of the antenna coil to provide further protection from Corrosion and erosion. Alternatively, the standoff sleeve 38, coil 40, and positioning sleeves 42, 44 can be made as a unitary piece. Also, other shaped RF coils can be used.

For a downhole tool, the outer diameter of the magnet assembly 14 is preferably less than the inner diameter of the tool housing. In addition, if Pulsed Field Gradient (PFG) diffusion measurements are to be made on the fluids in the flowline, the magnet assembly 14 must have a bore 26 (i.e., hole through the center) large enough to accommodate both the first flowline 24 and a pair of gradient coils 28 that are exterior to the flowline 24. The bore 26 diameter must be large enough so that the gradient coils 28 are not too close to the inner wall of the magnet carrier 16. Otherwise eddy currents induced in the magnet carrier 16 and surrounding metals will interfere with the efficiency of the PFG coils 28 and thereby adversely affect the spin echo measurements. Eddy current effects in PFG experiments are known to change the phase (i.e., the ratio of the real and imaginary data) of the spin echo. In practice, the instrumented (first) flow tube 24 and the PFG coils 28 (if any) are manufactured as a replaceable cylindrical module having an outside diameter very close to the inside diameter of the magnet assembly bore 26. Thus, one can easily exchange between different RF and PFG coils, as desired.

The magnet cover 22 is a cylindrically shaped outer sleeve made from high magnetic permeability material such as magnetic stainless steel or cold roll steel. The magnet cover 22 is an outer housing of the magnet assembly 14. The magnet cover 22 provides a return path for the magnetic flux, confining the magnetic field so that it is relatively weak outside of the magnet assembly 14. This is important because a strong magnetic field in the region outside the magnet assembly 14 could cause magnetic metal debris from the drilling mud to stick to the outer surface of the tool housing, which could adversely affect the field in the measurement region.

A preferred embodiment of the invention has a small diameter magnet assembly 14 that has a small magnetic field gradient over the measurement volume. The small gradient is desirable to minimize diffusion effects on spin-spin ($T_2$) relaxation time measurements that may be due to an inhomogeneous static magnetic field.

Tools used in well logging can be subjected to high levels of shock during transportation to and from a wellsite and during logging operations. The mechanical stability of the entire NMR module, as well as the magnet and the RF section, during and after shock is important for survival in the downhole environment. The integrity of the NMR measurements requires that the individual magnet pieces be constrained from moving or shifting during shock. The magnet assembly 14 must be capable of withstanding the high temperatures, pressures, and shocks encountered in a downhole environment.

It is understood that minor modifications to the detailed design discussed here, including using larger magnets, can be made to achieve a higher magnetic field strength. The higher field strength can be used to provide a higher signal-to-noise ratio for the NMR measurements. The present invention also provides a fill factor of close to unity so as to maximize the S/N of the NMR measurements. Having a high S/N is crucial for borehole measurements because it reduces the time required for making robust NMR measurements. Time savings translate into valuable savings in rig-time costs.

Gradient coils for performing pulsed field gradient diffusion measurements are situated on the outside of the first flowline 24. The gradient coils can be placed outside of the metal flowline because the gradient coils 28 are energized by direct current pulses and therefore produce a static magnetic field component, which easily penetrates the non-magnetic metal flowline. The pulsed field gradient coils 28 are preferably two elongated multi-turn quadrupole coils that are placed outside of and in close proximity to the first flow tube 24 in diametrically opposed positions (i.e., their angular separation is 180 degrees). The two gradient coils are held in place, for example, by ceramic fixtures with screws holding the two opposing fixtures together. It is possible to construct the fixtures using other non-magnetic materials, including metals. The gradient coils 28 are oriented so that the direction of the pulsed field gradient is parallel to the static magnetic field produced by the magnet 20. Gradient coil types other than quadrupole coils can also be used.

The first flowline 24 and associated antennas provide high S/N measurements of fluids in the sensitive region of the RF coil 40. Placing the RF antenna 40 inside the flowline 24 actually enhances the S/N because the antenna fill factor (i.e., ratio of fluid volume to interior volume of the RF coil) is essentially unity. The PFG coils 28 can be placed inside or outside the metal flow line, but placing the PFG coils outside the first flow tube conserves the limited available space inside of the first flowline 24. Also, the wires that connect the gradient power supply to the gradient coil antennas are more easily accessible and do not have to be routed from outside to inside the flowline through a pressure sealing feed through.

Figure 4:
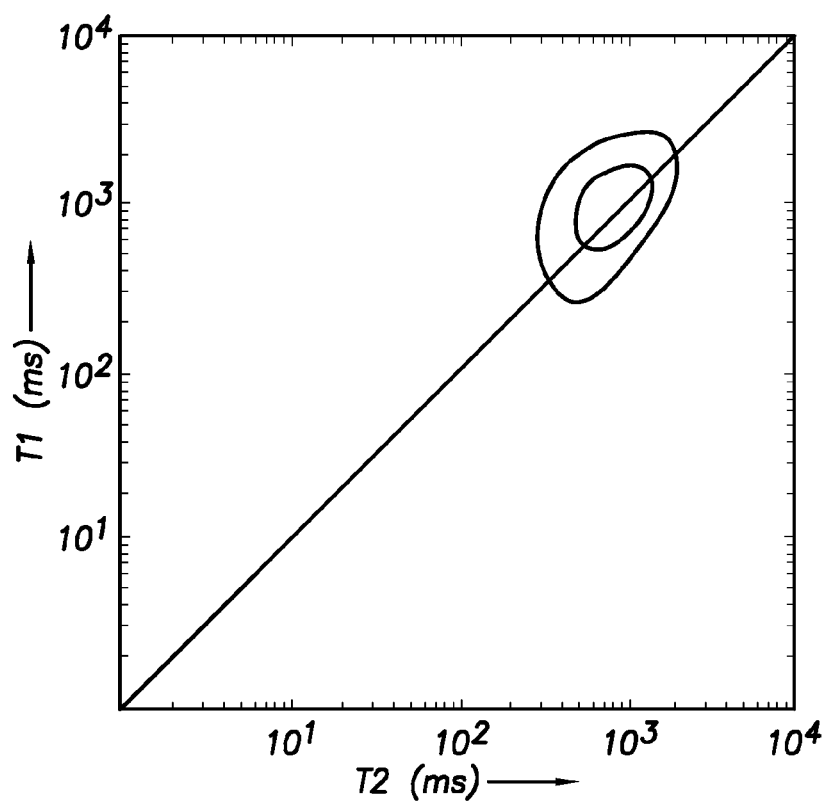
FIG. 4 is a two-dimensional map showing signal amplitudes versus longitudinal (T1) and spin-spin (T2) relaxation times, as can be produced using the high pressure/high temperature magnetic resonance tool of FIG. 1.

The permanent magnet that surrounds the flowline 24 and the antennas provides the static magnetic field that is used to polarize the NMR sensitive nuclei in the fluids. The NMR and fluid properties that can be derived from measurements in the metal flowline 24 include: (1) hydrogen indices of fluids derived from signal amplitude measurements, (2) spin-spin relaxation time distributions derived from the decay of the transverse magnetization, (3) longitudinal relaxation time distributions derived, for example, from the polarization time dependence of the signal amplitudes, (4) diffusion coefficient distributions derived, for example, from pulsed field gradient signal amplitude attenuation measurements, and (5) chemical shift spectra. Measurement of chemical shift spectra requires a magnet with a substantially uniform magnetic field over the NMR sensitive volume of the RF antenna. The NMR measurements can be used to derive various two- and three-dimensional maps of signal amplitudes as a function of spin-spin relaxation times, longitudinal relaxation times, and diffusion coefficients. FIG. 4 shows a two-dimensional map of signal amplitudes as a function of spin-spin and longitudinal relaxation times. The one-dimensional T1 and T2 distributions can be computed from the map by summing amplitudes along the x or y axis, respectively. U.S. Pat. No. 7,053,611 teaches inversion of NMR measurements to produce multi-dimensional maps and is incorporated by reference for all purposes.

The foregoing has outlined rather broadly the features and technical advantages of the present invention so that the detailed description of the invention may be better understood. Additional features and advantages of the invention will be described hereinafter which form the subject of the claims of the invention. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the scope of the invention as set forth in the appended claims.

What is claimed is:

1. An apparatus to perform magnetic resonance measurements on a high temperature and/or high pressure sample, comprising:
   a first flow tube having a longitudinal axis and an interior region, and containing the high temperature and/or high pressure sample;
   a pair of parallel magnetic plates disposed on opposite sides of the first flow tube and being magnetized perpendicular to the first flow tube longitudinal axis;
   an antenna disposed in the interior region of the first flow tube; and
   pulsed field gradient coils disposed in close proximity to but outside of the first flow tube.

2. The apparatus of claim 1, wherein the magnetic resonance measurement is a nuclear magnetic resonance measurement or an electron spin resonance measurement.

3. The apparatus of claim 1, wherein the sample is formation fluid or process fluid.

4. The apparatus of claim 1, wherein the first flow tube is made of metal.

5. The apparatus of claim 1, wherein the magnetic plates comprise one or more pieces of permanent magnetic material.

6. The apparatus of claim 1, further comprising a magnet assembly, wherein the magnet assembly carries the pair of magnetic plates.

7. The apparatus of claim 6, wherein the magnet assembly comprises an outer housing having a high magnetic permeability.

8. The apparatus of claim 6, wherein the magnet assembly comprises a thru-wire passageway through which wires pass.

9. The apparatus of claim 6, wherein the magnet assembly comprises a first flow tube passageway through which the first flow tube passes.

10. The apparatus of claim 6, wherein the magnet assembly comprises a second flow tube passageway through which a second flow tube passes.

11. The apparatus of claim 6, wherein the magnet assembly comprises one or more pole pieces disposed between the magnetic plates and the first flow tube.

12. The apparatus of claim 6, wherein the magnet assembly comprises a magnet carrier on which the magnetic plates are mounted, an outer housing having a high magnetic permeability, and magnet pole pieces.

13. The apparatus of claim 12, wherein the magnet carrier has a first bore through which the first flow tube passes, a second bore through which a second flow tube passes, and a third bore through which wires pass.

14. The apparatus of claim 1, wherein the antenna is a coil disposed between a stand-off layer and a protective layer.

15. A method to perform magnetic resonance measurements on a high temperature and/or high pressure sample, comprising:
    providing a first flow tube having a longitudinal axis, an interior region, and containing the high temperature and/or high pressure sample, a pair of parallel magnetic plates disposed on opposite sides of the first flow tube and being magnetized perpendicular to the first flow tube longitudinal axis, an antenna disposed in the interior region of the first flow tube; and pulsed field gradient coils disposed in close proximity to but outside of the first flow tube;
    polarizing the sample using the pair of magnetic plates;
    generating one or more electromagnetic field pulses using the antenna;
    receiving a magnetic resonance signal from the sample; and
    determining the measurement from the received signal.

16. The method of claim 15, wherein the magnetic resonance measurements are nuclear magnetic resonance measurements or electron spin resonance measurements.

17. The method of claim 15, further comprising deriving one or more of a T1 distribution, a T2 distribution, a diffusion coefficient distribution, and a hydrogen index of the sample.

18. The method of claim 17, wherein the distributions and hydrogen index are derived from one or more multi-dimensional maps.

19. The method of claim 15, further comprising using the Q of the antenna to determine conductivity of the sample.

20. The method of claim 15, further comprising determining a fluid velocity profile.

21. The method of claim 15, further comprising stopping fluid flow and making measurements on the stopped fluid.

* * * * *